(12) United States Patent
Evans et al.

(10) Patent No.: US 8,021,617 B2
(45) Date of Patent: Sep. 20, 2011

(54) FLUE GAS MONITORING AND DYNAMIC SPIKING FOR SULFUR TRIOXIDE/SULFURIC ACID

(75) Inventors: Scott A. Evans, Ingleside, IL (US); Daniel H. Roesler, Houston, TX (US)

(73) Assignee: Clean Air Engineering, Inc., Palatine, IL (US)

( * ) Notice: Subject to any disclaimer, the term of this patent is extended or adjusted under 35 U.S.C. 154(b) by 82 days.

(21) Appl. No.: 12/606,454

(22) Filed: Oct. 27, 2009

(65) Prior Publication Data

US 2011/0097809 A1   Apr. 28, 2011

(51) Int. Cl.
*G01N 33/00* (2006.01)
(52) U.S. Cl. .......... 422/93; 436/102; 436/119; 436/122; 422/83
(58) Field of Classification Search .................. None
See application file for complete search history.

(56) References Cited

U.S. PATENT DOCUMENTS

| | | | |
|---|---|---|---|
| 4,279,618 A * | 7/1981 | Barden | 436/102 |
| 4,319,966 A * | 3/1982 | Carlson et al. | 205/785 |
| 4,343,768 A | 8/1982 | Kimura | |
| 5,338,515 A | 8/1994 | Dalla Betta et al. | |
| 6,399,391 B1 | 6/2002 | Tomlin | |
| 7,029,920 B2 | 4/2006 | Lanier et al. | |
| 7,562,556 B2 | 7/2009 | Johnston et al. | |
| 2005/0233463 A1 | 10/2005 | Dominelli et al. | |
| 2010/0284899 A1* | 11/2010 | Kita et al. | 423/522 |

OTHER PUBLICATIONS

A. Jain, Method 8A—Determination of Sulfuric Acid Vapor or Mist and Sulfur Dioxide Emissions From Kraft Recovery Furnaces, National Council of The Paper Industry for Air and Stream Improvement (Dec. 1996).

* cited by examiner

*Primary Examiner* — Yelena G Gakh
*Assistant Examiner* — Michelle Adams
(74) *Attorney, Agent, or Firm* — Quarles & Brady LLP

(57) ABSTRACT

Systems and methods are disclosed for measuring sulfur trioxide/sulfuric acid content of flue gas. A probe is provided that extracts two separate lines of gas samples simultaneously from the flue gas. One of the two lines is dynamically spiked with a known quantity of sulfur trioxide, preferably generated in the probe. A comparison of sulfur trioxide/sulfuric acid content measurements from the spiked and unspiked lines helps identify and adjust for inherent biases in the measuring system. Also disclosed are catalyst structures and methods for use thereof for generating sulfur trioxide at known concentration.

2 Claims, 7 Drawing Sheets

$$m_{spike} = c_{spike} \cdot \dot{m}_{spike} \cdot t \cdot eff$$

WHERE:

$m_{spike}$ = MASS OF $SO_3$ SPIKE $c_{spike}$ = CONCENTRATION OF $SO_2$ INJECTED $\dot{m}_{spike}$ = MASS FLOW RATE OF $SO_3$ SPIKE t = DURATION OF SPIKE eff = CONVERSION EFFICIENCY OF CATALYST $$\text{RECOVERY} = \frac{m_{\text{spiked side}} - \left[ m_{\text{unspiked side}} \cdot \dfrac{\left(V_{\text{spiked side}} - V_{\text{spike}} - V_{\text{purge}}\right)}{V_{\text{unspiked side}}} \right]}{m_{\text{spike}}}$$

WHERE:

RECOVERY = PERCENT RECOVERY OF SPIKE $m_{\text{spiked side}}$ = MASS OF $SO_3$ COLLECTED FROM SPIKED SIDE TRAIN $m_{\text{unspiked side}}$ = MASS OF $SO_3$ COLLECTED FROM UNSPIKED SIDE TRAIN $m_{\text{spike}}$ = MASS OF $SO_3$ SPIKE $V_{\text{spiked side}}$ = STANDARD VOLUME OF GAS COLLECTED FROM SPIKED SIDE TRAIN $V_{\text{unspiked side}}$ = STANDARD VOLUME OF GAS COLLECTED FROM UNSPIKED SIDE TRAIN $V_{\text{spike}}$ = STANDARD VOLUME OF SPIKE GAS $V_{\text{purge}}$ = STANDARD VOLUME OF PURGE GAS

FIG. 8

FLUE GAS MONITORING AND DYNAMIC SPIKING FOR SULFUR TRIOXIDE/SULFURIC ACID

CROSS-REFERENCE TO RELATED APPLICATION

Not applicable.

STATEMENT OF FEDERALLY SPONSORED RESEARCH OR DEVELOPMENT

Not applicable.

BACKGROUND OF THE INVENTION

The present invention relates to measuring air pollutant emissions from combustion sources which burn sulfur containing materials (e.g. coal fired power plants). More particularly the invention relates to monitoring systems (and related methods) which can measure sulfur trioxide/sulfuric acid levels in such flue gas.

Power plants and many other facilities are usually required to keep emissions of exhaust gases below specified levels, and further often required to monitor and periodically report to appropriate regulatory agencies their performance in doing so. If the fuel they use contains sulfur (as is typical for coal and some oil-based fuels), sulfur oxides will be produced as a byproduct of the combustion. Of those sulfur oxides, approximately 0.7% is typically sulfur trioxide.

Further, other downstream pollutant removal devices, such as nitrous oxide control devices, may alter the relative amount of sulfur dioxide to sulfur trioxide. Also, if (as is typical) there is moisture/humidity in the exhaust stack, sulfur trioxide will convert in the stack to sulfuric acid.

Where the plant tries to avoid exceeding emissions limits by using low sulfur fuels (without special capture equipment), it is desirable to monitor the exhaust stack to confirm that the fuel in fact has sulfur levels that are sufficiently low so as to avoid the need for using sulfur oxide removal technologies. Where higher sulfur fuels are used, and sulfur oxide removal technologies are applied upstream of the exhaust stack, it is still desirable to periodically monitor the success of the removal technologies (e.g. to spot maintenance issues).

Sulfur trioxide is of particular concern because it is aggressively hygroscopic and will quickly form sulfuric acid in the presence of humidity. As is well known, releasing substantial amounts of sulfuric acid into the air can cause significant adverse impacts as a condensable particulate. Also, sulfuric acid can affect mercury control systems and corrode duct work and other equipment.

Hence, there have been extensive efforts to measure sulfur trioxide/sulfuric acid levels in flue gas. A standard method of measurement is to extract samples of gas from the flue, provide the sample with sufficient moisture to convert all sulfur trioxide in it to sulfuric acid, condense the sulfuric acid, and measure the quantity of sulfuric acid collected in a given extracted sample (e.g. by using ion chromatography). While this works reasonably well when measuring relatively high concentrations of sulfur trioxide/sulfuric acid, it is susceptible to significant bias when measuring relatively low concentrations. This is of increasing concern because permitted regulatory emission levels are dropping over time, increasing the need for accuracy at low concentration measurements.

The error/bias problem is compounded when the sample is a complex variable mix of flue gas with particulate. Clogging and/or premature condensing problems due to this can distort the accuracy of various known measurement equipment.

In U.S. Pat. No. 7,029,920 it was proposed to sample stack gas using a probe projecting into the stack. Rather than shutting the normal sampling off completely periodically for calibration, this patent instead taught, on a periodic basis, testing sample gas mixed with a known amount of spiked nitrogen oxide containing gas, and then using the resulting measurement to try to assess bias when measuring nitrogen oxides.

However, this system required one to assume that the flue gas contaminant content was essentially the same at the time of unspiked sampling as when spiked sampling was happening before or thereafter, and spiking was focused on nitrogen oxide gas measurements. Further, it relied on a readily available supply of nitrogen oxide based spiking gas of reliable concentration. Also, it required an external construction to accommodate the spiking gas source. This system is not readily adaptable for assessing sulfur trioxide/sulfuric acid measurement variability, and still had some unaccounted for biases.

One problem in applying this approach to sulfur trioxide/sulfuric acid testing is there exists no readily available source of sulfur trioxide gas with carefully controlled concentration values, and hence a reliable "known" is currently unavailable as a practical matter. One could generate sulfur trioxide from commercially available sources of sulfur dioxide, and then use that sulfur trioxide for calibration. However, techniques have not yet been reported for reliably producing a known supply with a sufficiently stable concentration of sulfur trioxide for this purpose.

Thus, a need exists for improvements in the equipment and methods used to monitor flue gas for small concentrations of sulfur trioxide/sulfuric acid.

SUMMARY OF THE INVENTION

The present invention provides a system for monitoring sulfur trioxide/sulfuric acid levels in an emission stream flowing through an exhaust. The system has a probe positionable relative to the exhaust to be able to extract essentially simultaneously both a first supply train of sample gas from the exhaust and a second supply train of sample gas from the exhaust. There are means for measuring the amount of sulfur trioxide/sulfuric acid in the first supply train, and a means for supplying sulfur dioxide gas of a known quantity to a catalyst, converting that sulfuric dioxide gas that has been supplied to the catalyst to sulfur trioxide gas, spiking the second supply train with the catalyst converted sulfur trioxide gas to create a spiked train, and then measuring the amount of sulfur trioxide/sulfuric acid in the spiked train. The system is configured such that a comparison of the results of the two measurements can help validate the system.

By "sulfur trioxide/sulfuric acid" we mean the amount of sulfuric acid in the sample being measured (including any spiking) once any sulfur trioxide in the sample and any spiked amount of sulfur trioxide have been converted to sulfuric acid.

In preferred forms:

(a) a probe houses a catalyst that is capable of converting sulfur dioxide gas to sulfur trioxide gas;

(b) the catalyst is platinum based;

(c) heating coils are positioned adjacent to the catalyst which can heat the catalyst to a temperature above 750° F. (e.g. between 750° F. and 850° F.), with thermocouples provided in the probe for controlling this; and (d) the probe has an inlet line for feeding sulfur dioxide gas to the catalyst, a carrier line for carrying sulfur trioxide gas from the catalyst to a connection to the second sample train, and an outlet line for carrying sulfur trioxide spiked vapor to a connector to measuring equipment, and a line for carrying an unspiked sample of flue gas.

In another form the invention provides a method of monitoring sulfur trioxide/sulfuric acid levels in an emission stream flowing through an exhaust. The method involves placing a probe relative to the exhaust so as to extract essentially simultaneously both a first supply train of sample gas from the exhaust and a second supply train of sample gas from the exhaust. One then:

(a) measures the amount of sulfur trioxide/sulfuric acid in the first supply train;

(b) spikes the second supply train with a known quantity of sulfur trioxide gas;

(c) measures the amount of sulfur trioxide/sulfuric acid in the spiked train; and (d) then compares results of the two measurements.

The present invention creates a unique way of generating a supply of spiking gas with a reliable known concentration of sulfur trioxide. Because it is generated close to the inputs for the exhaust samples, it is less susceptible to distortions not present in the unspiked line. The system allows simultaneous measurements of spiked and unspiked lines.

The preferred way of measuring sulfuric acid in a sample is to filter particulate out of each sample at an elevated temperature of about 600° F. in an oven, and then running the resultant through a condenser at a temperature above water temperature condensation temperatures, but below sulfuric acid condensation levels. The sulfuric acid is condensed/collected on glass wool or other filter material, and the collected glass wool and other filter material is analyzed for sulfuric acid content in a conventional ion chromatography system.

For other techniques for evaluating sulfur trioxide levels from a train of sample gas see generally A. Jain, Method 8A—Determination Of Sulfuric Acid Vapor Or Mist And Sulfur Dioxide Emissions From Kraft Recovery Furnaces, National Council Of The Paper Industry For Air And Stream Improvement (December 1996). See also EPA Methods 8 and 8A.

Because a particular sampling probe needs to be shut off while the glass wool and other collectors in the condenser are being removed for analysis, this method is not a continuous method if just one pair of collectors is used. In this regard, after completing each run, the contents of the sulfuric acid condensers are preferably washed to collect their sulfate contents, which can then be analyzed. Each run can monitor for about an hour if desired. A back-up pair of collectors can be used during this process to provide a more continuous system.

The remnant sample not condensed in the sulfuric acid condenser can be used for testing sulfur dioxide levels if desired, and would be linked to a vacuum source and meter to establish the negative pressure needed to withdraw samples, in order to measure how much flow is occurring in a given period.

The system can spot sulfur content problems in fuel sources (e.g. combustion ratio accuracy of sulfur trioxide production), problems in sulfur oxide removal equipment, and developing problems in the measuring equipment. The system also provides accurate measurements even when the stack contains only very low concentrations of sulfur trioxide/sulfuric acid.

These and still other advantages of the present invention will become more apparent, and the invention will be better understood, by reference to the following description of the preferred embodiments of the present invention taken in conjunction with the accompanying drawings.

BRIEF DESCRIPTION OF THE DRAWINGS

FIG. 8 is a formula useful in calculating measurements.

DETAILED DESCRIPTION OF THE PREFERRED EMBODIMENTS

Figure 1:
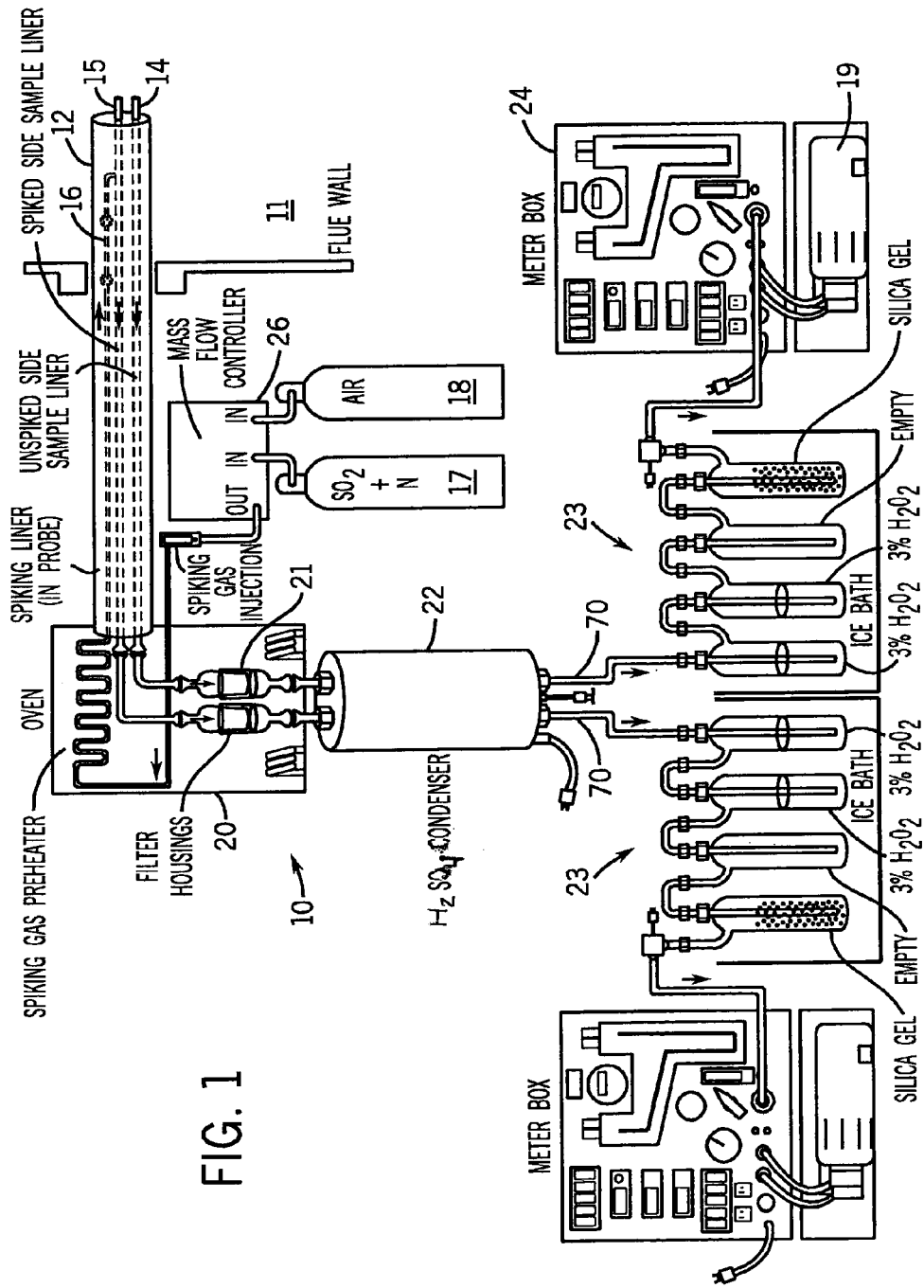
FIG. 1 is a schematic flow diagram for a representative portion of a preferred monitoring system of the present invention.

FIG. 1 depicts a monitoring system, generally 10, for monitoring sulfur trioxide/sulfuric acid levels in the exhaust gas of a flue stack 11. There is a probe 12 inserted through a wall of the stack into the exhaust stream. It is configured to extract two separate supply trains of exhaust gas simultaneously, albeit from inlets in very close proximity to each other.

As previously noted, the preferred means of measuring sulfur trioxide/sulfuric acid levels using this system is to convert sulfur trioxide gas in the sample gas to sulfuric acid due to the presence of humidity in the exhaust gas, and then measure the quantity of sulfuric acid in the resultants. As depicted in FIG. 1, there is a first sampling line 14 that can continuously extract a train of exhaust from the stack. There is also a second sampling line 15 that can extract a second supply of samples of the exhaust. This latter train is spiked slightly downstream of the inlet to line 15 with a known amount of sulfur trioxide. The sulfur trioxide used for spiking is generated within the probe itself.

After the sulfur trioxide in the gas samples (plus the spiking sulfur trioxide where added) have been converted to sulfuric acid, the amount of total sulfuric acid is measured, and the results are compared. If the difference between the two readings is lower than one would expect due to the known spiking amount, the difference below the spiking amount can be used generate a percentage error/bias, and that then can be used to correct the unspiked reading.

Because the samples are taken from locations so close to one another, and essentially simultaneously, sources of variability due to differences in the flue content over time, or due to differing locations for extraction, are minimized. Further, this equipment can be operated without any need to interrupt continuous monitoring.

Further, we overcome the lack of readily available sulfur trioxide having reliably consistent concentrations by generating the gas on site under carefully controlled conditions. We have discovered an optimal temperature range for sulfur dioxide/sulfur trioxide catalytic conversion, means to maintain that temperature, and positioning of the conversion very close to the spiking point. We have also developed protocols for "seasoning" the catalyst to avoid distortions due to catalytic absorption of sulfur dioxide during start-up. As a result, our known used for spiking is remarkably consistent in concentration.

We prefer a platinum catalyst (e.g. platinum coated alumina) 16. However, other catalysts may also be suitable, such as a vanadium pentoxide based catalyst. We particularly prefer to pre-heat sulfur dioxide mixed with an oxygen source such as air to about 800 degrees Fahrenheit (750-850° F.) before it passes into the catalyst.

Immediately after the sulfur trioxide is generated in the catalyst, it is released adjacent the inlet of sampling line 15. Because this line is under vacuum due to pump 19, all of the spiking sulfur trioxide generated is reliably pulled through that line and then subjected to all of the same biasing factors that the exhaust gas is.

Key features of the equipment are the probe 12, an oven 20 upstream of the probe, filters 21, a sulfuric acid condenser 22, impinger sets 23 for measuring sulfur dioxide, a pump 19, and a dry gas meter 24. There is also a cylinder 17 containing a sulfur dioxide/nitrogen mix, and another cylinder 18 containing air, along with a multi-gas mass flow controller/mixer 26.

Figure 2:
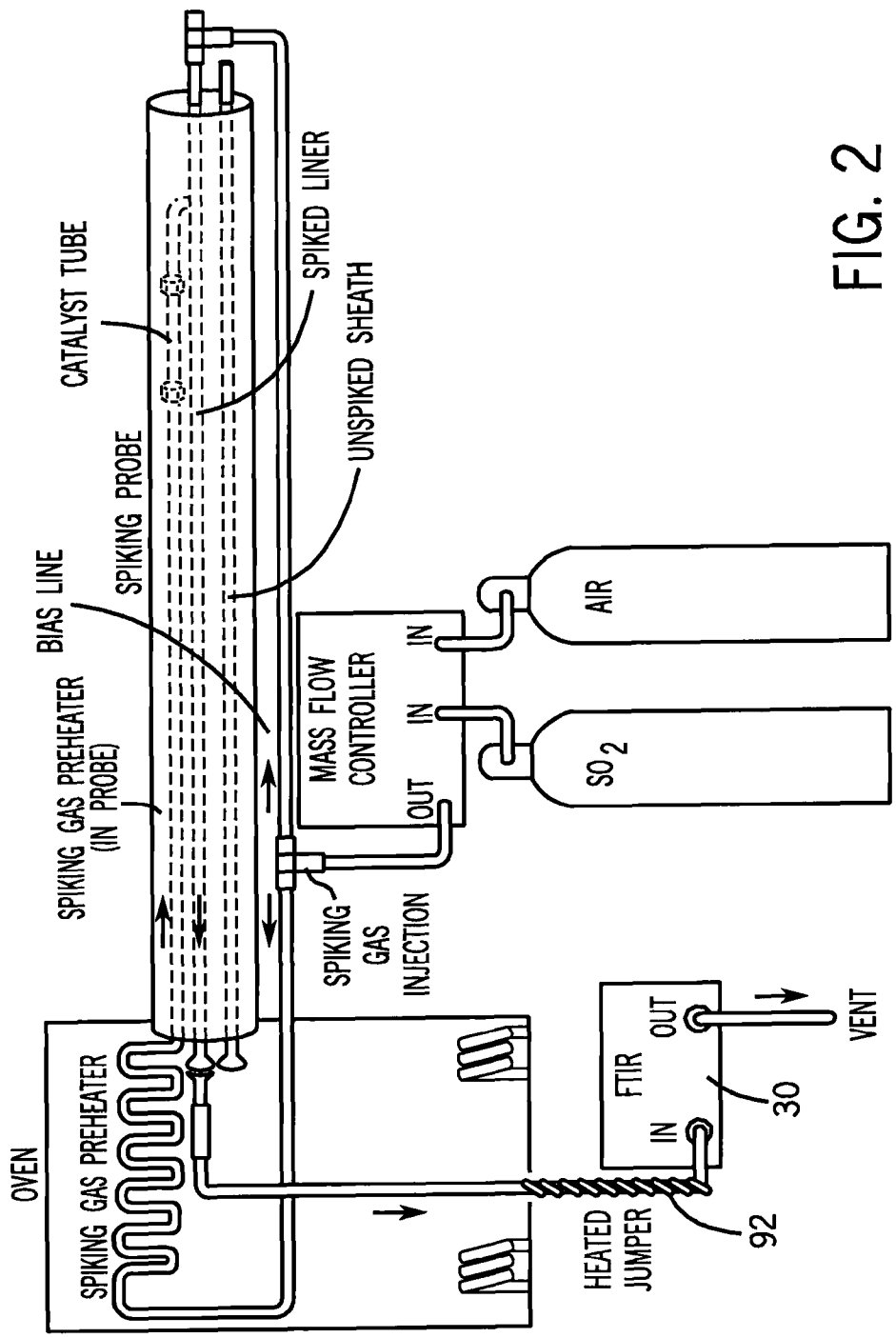
FIG. 2 shows a portion thereof during a conversion efficiency set-up check.

FIG. 2 depicts a preferred set-up of the equipment when checking conversion efficiency prior to actual exhaust sampling. There is a Fourier Transform Infrared Spectrometer (FTIR) 30 or similar instrument to verify catalyst conversion efficiency.

The probe still houses the two sampling lines, the spiking line, and the catalyst tube. The probe is typically about ten feet long and has a cam-and-groove fitting at its downstream end. This allows enough heating time of flue gas sample so sulfuric acid that might have otherwise condensed inside the probe will vaporize.

Inside the probe shell there are two liner sheaths into which the sampling lines slide. The spiking line sheath is larger than the unspiked line sheath so it can accommodate both the spiking line and the spiked-side sampling line. The probe is heated via coil heaters wrapped around the two sampling line sheaths, and the shell of the probe is insulated with ceramic paper insulation.

Two thermocouples 40/41 monitor the internal temperature of the probe at four and eight feet from the downstream end. One thermocouple 42 travels the length of the probe and comes out the upstream end of the probe to monitor the flue gas temperature entering the sampling systems.

The catalyst tube is attached to the spiking line. The spiked-side sampling line has an injection point 43 approximately nine inches back from the probe tip that turns and is pointed downstream in parallel with the sampling line. This injection point is where the catalyst tube attaches. When attached the catalyst tube and spiking line run in parallel with the spiked-side sampling line the entire length of the probe.

The catalyst tube and the spiking line can be made of one half inch diameter stainless steel, and the spiked-side sampling line (and injection point) can be made of quartz glass or another non-reactive substance (such as titanium). The fitting used to attach the injection point to the catalyst tube can be a stainless steel one half inch fitting with a graphite ferrule. The graphite ferrule ensures that the link between the catalyst tube and the injection point is sealed and highly temperature resistant.

There are baffles 50 of ceramic paper insulation (about one inch long) wrapped around the spiking line along its length to prevent it from colliding with the spiked-side sampling line (potentially breaking the quartz). When assembled the spiked side sampling line, catalyst tube, and spiking line reside inside the spiked-side sheath of the probe. They can be removed from the sheath by sliding the parallel lines out the downstream side of the probe.

The unspiked-side sampling line is made of quartz or another non-reactive substance and has no injection point. It also slides easily out of the unspiked-side sheath in the probe. The probe is attached to the oven (via a cam-and-groove lock) which houses connection points for the heating coils (electrical connections) and thermocouples (thermocouple connections). All fittings are high temperature resistant fittings.

One additional purpose of the oven is to heat the particulate filters 21 for the sulfuric acid test methods above sulfuric acid's condensation point so it will pass through the particulate filters. The particulate filter housings for both the spiked-side and unspiked side are joined to their respective sampling lines. Both the filter housing and particulate filter substrate can be made of quartz glass. If another non-reactive filter housing material is available, it may be substituted for quartz.

Inside the oven is also an additional sulfur dioxide pre-heating coil. The current model is a racetrack-style double coil, but other styles of coils could be used depending on space available. The attachment point for the multigas mass flow controller/mixer goes through the wall of the oven and into the sulfur dioxide pre-heating coil. The filter housings exit out of the oven and go to the sulfuric acid condenser.

The sulfuric acid condenser contains two parallel condensers, one for the spiked-side sampling train, and one for the unspiked-side sampling train. The purpose of the sulfuric acid condenser is to condense out the sulfuric acid present in the sampling train while allowing other substances such as sulfur dioxide and water vapor to pass through.

We prefer a sulfuric acid condenser which has a straight-through Pyrex tube containing a length of glass wool to catch condensed sulfuric acid. The condenser is held at a temperature of 150 degrees Fahrenheit.

Another potential style of condenser may involve a condensing coil and filter or frit held at 150 degrees Fahrenheit. The sulfuric acid condenser style, however, should be the same on both the spiked-side and unspiked-side sampling trains. Once the system has operated for a defined period (e.g. one hour), the filters are removed, and processed for measurement as noted above.

The gas exiting the condenser at 70 then passes to impinger sets 23 for each sampling train. They are held at less than 68 degrees Fahrenheit to condense out moisture from the flue gas stream. These impinger sets are attached downstream of the sulfuric acid condensers.

The impinger sets may also include a three percent hydrogen peroxide solution to react with sulfur dioxide to provide a separate sulfur dioxide measurement avenue for the flue gas via a modified Greenburg-Smith impinger (straight-through stem), followed by three percent hydrogen peroxide in a standard Greenburg-Smith impinger (restricted stem), followed by an empty modified Greenburg-Smith impinger (straight through stem), followed by a modified Greenburg-Smith impinger (straight through stem) filled with silica gel.

Downstream of the impinger sets, each sampling train is attached to the dry gas pump 19 and meter 24. The purpose of these pump and meters is to establish the negative pressure to effectuate the sampling, and to also measure the quantity of gas being pulled through the system. The volume collected is converted into a standard dry volume measurement by measuring the average temperature of the dry gas meter. Bypass valves on the pumps determine the rate at which the pumps pull flue gas through each sampling train.

Figure 3:
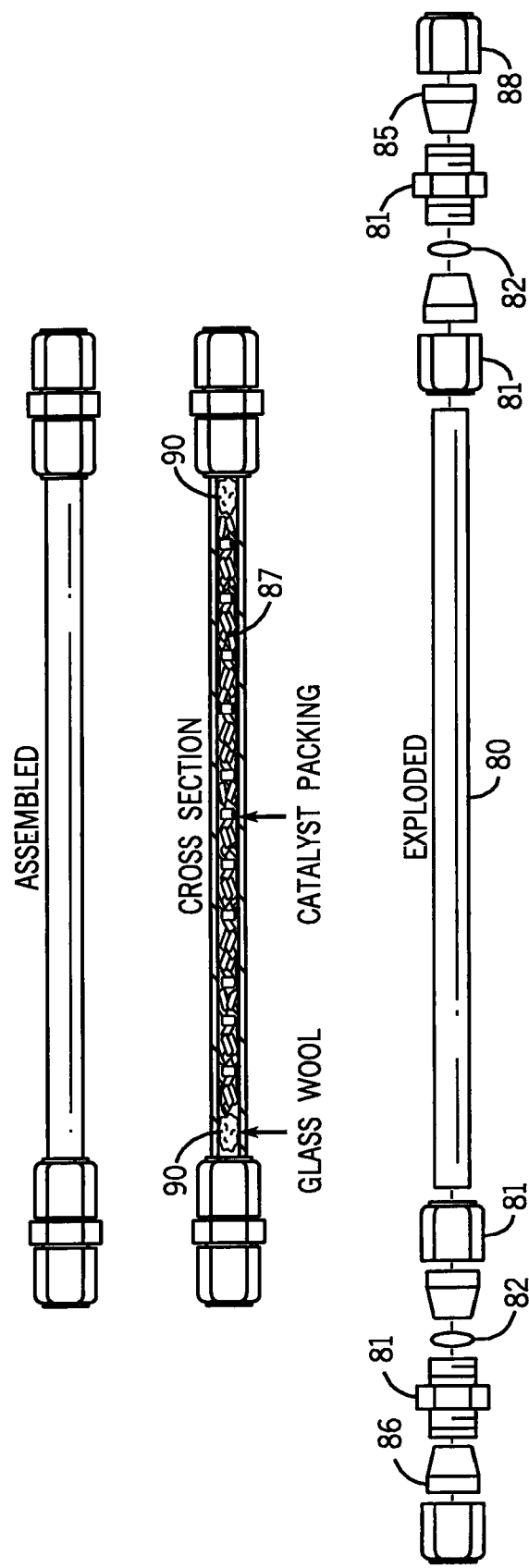
FIG. 3 shows three different views of a preferred catalyst tube of the present invention.
Figure 4:
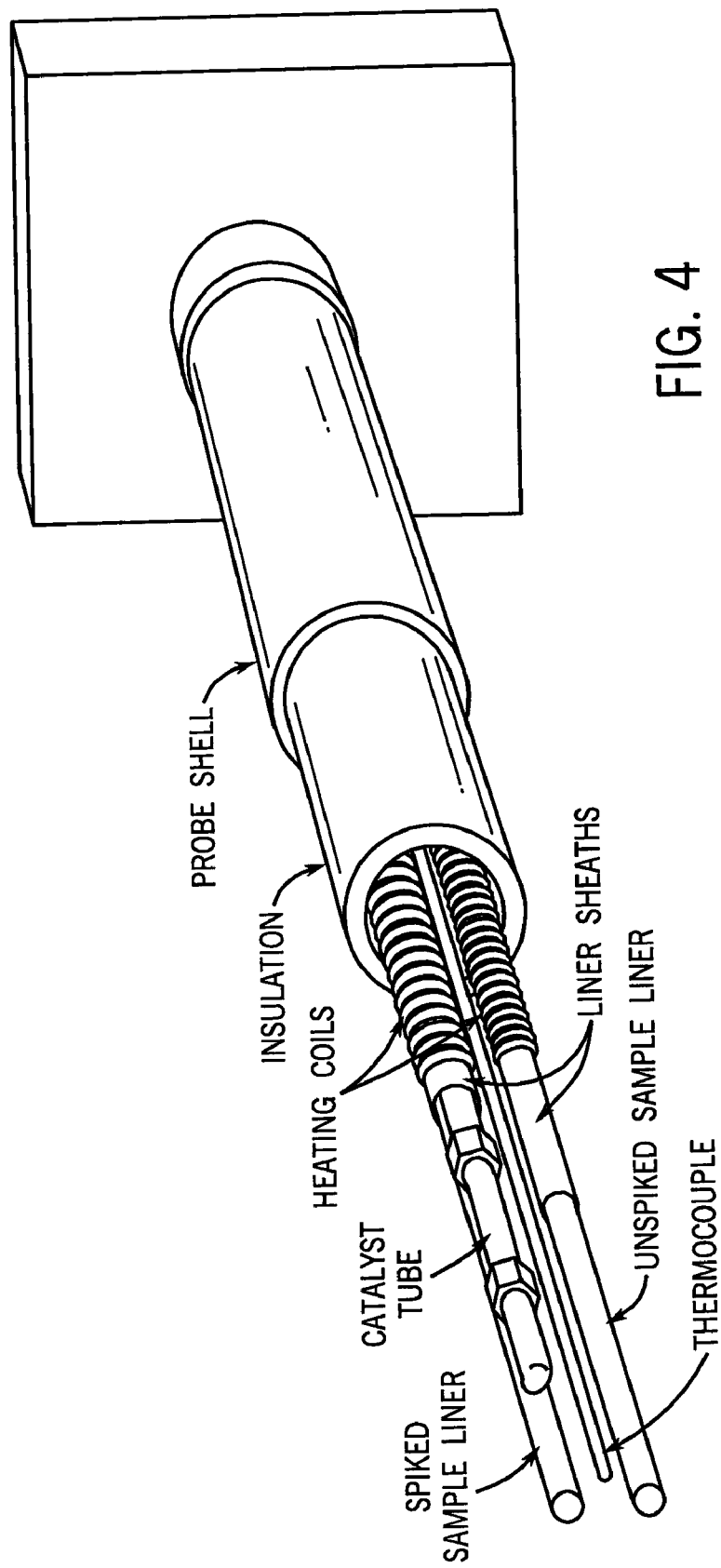
FIG. 4 is a cutaway perspective view of the probe useful therewith.
Figure 5:
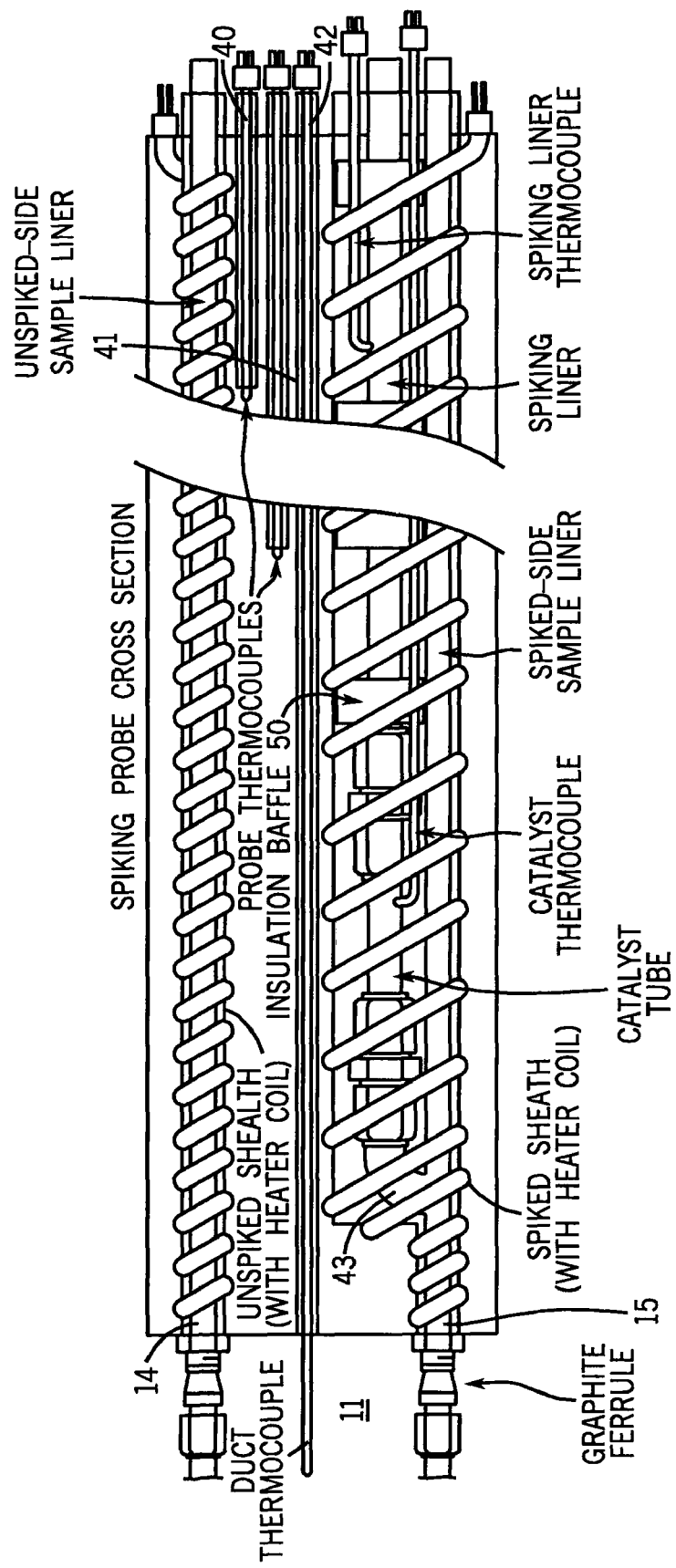
FIG. 5 is a fragmentary cross sectional view taken through the FIG. 4 probe.

The following is a more detailed description of the catalyst tube associated with the probe used for converting sulfur dioxide to sulfur trioxide. As best seen in FIG. 3, there is a one half inch diameter stainless steel tube 80 (0.035 inch wall thickness about eleven inches long). On each end of the tube stainless steel unions 81 are placed to allow the tube to be connected to other components. Between the tube and unions on both ends are round stainless steel mesh plates 82 that are compressed between the unions and the tube.

These mesh plates prevent the catalyst packing from falling out either end of the tube. One end of the catalyst tube is connected with a stainless steel nut 88 and stainless steel ferrule 85 to the stainless steel spiking liner. The other end of the catalyst tube is connected to the injection point on the spiked-side sample liner with a stainless steel nut 88 and graphite ferrule 86.

The tube contains the catalyst packing 87. For this invention's testing, around sixteen grams of 3.2 mm alumina pellets coated with one percent by mass platinum were used as the catalyst packing. Approximately one half inch of glass wool 90 was used on each end of the catalyst packing to prevent the pellets from banging up against the mesh plates. The catalyst tube could be used in either direction since it is symmetrical, just as long as a graphite ferrule is used to attach the catalyst tube to the injection point on the spiked-side sample liner.

Accurately using a catalyst on an alumina substrate requires a pre-conditioning period (which we call seasoning) for the catalyst to reach optimum conversion. Alumina adsorbs sulfur dioxide, so it must be first saturated with sulfur dioxide before one can assume a constant conversion rate of sulfur dioxide to sulfur trioxide for calibrating system bias. The seasoning of the alumina with platinum pellets must happen before the sulfur trioxide will be generated at a constant rate.

After the catalyst tube is seasoned, it will convert sulfur dioxide to sulfur trioxide at a constant rate as long as sulfur dioxide is flowed through the catalyst tube when it is heated into the optimum temperature range. The catalyst tube must be seasoned at the optimum temperature for the catalyst because the alumina's saturation point varies with temperature.

We then checked the conversion efficiency of the catalyst as shown in FIG. 2 using a Fourier Transform Infrared Spectrometer (FTIR) or other instrument capable of detecting sulfur trioxide to the back of the spiked-side sample line to measure the amount of sulfur trioxide produced by the catalyst. An FTIR can measure the concentration of sulfur trioxide, among other substances of a sample stream. However, sulfuric acid should not be allowed to condense inside the FTIR because it would cloud the mirrors and windows used for infrared absorption.

Since the FTIR operates at a temperature near the sulfuric acid condensation temperature, generated sulfur trioxide must not be allowed to form sulfuric acid vapor. This means keeping the sample stream for this check procedure free of moisture.

To check the conversion efficiency of the catalyst tube with the FTIR (or an equivalent sulfur trioxide measurement instrument), a heater 92 (a/k/a heated jumper) is connected between the spiked-side sampling line and the FTIR so the sulfur trioxide exiting the spiked-side sampling line is flowed directly into the FTIR. The probe tip is fitted with a gas line so the mass flow controller/mixer can flow gas either through the catalyst tube or bypass it.

The mass flow controller has a valve connected to it that directs the gas to be either flowed to the probe tip or through the catalyst. The conversion efficiency check is a closed system, using only cylinder gases (which have negligible moisture content), so the sulfur trioxide will not condense as sulfuric acid inside the FTIR. The sulfur trioxide concentration measured by the FTIR shows the conversion efficiency of the catalyst at temperature.

Figures 6, 7:
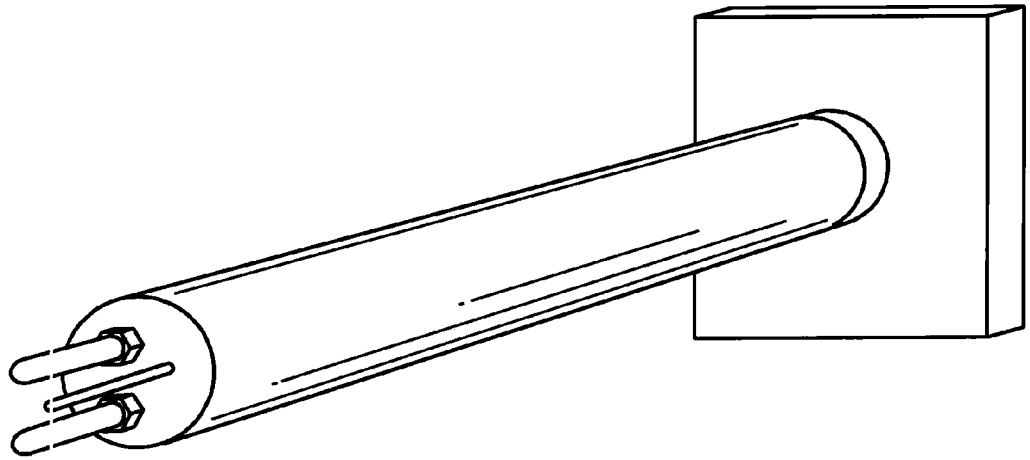
FIG. 6 is a top left side perspective view of a preferred probe of the present invention.
FIG. 7 is a formula useful in calculating spiking mass.

The optimal amount of sulfur trioxide spiked into a spiked-side sampling train depends on the length of time of the spike, conversion efficiency of the catalyst, the mass flow rate of the gas going into the catalyst tube, and the spiking gas sulfur dioxide concentration. See FIG. 7.

The recovery of the spike (%) is determined by comparing the unspiked-side sampling train sulfuric acid content to the spiked side sulfuric acid content (adjusting for volume differences). See FIG. 8.

To assemble a preferred catalyst tube, one needs a stainless steel tube, two stainless steel female unions, three stainless steel nuts and ferrules, one stainless steel nut and graphite ferrule, two stainless steel circular mesh plates, two glass wool plugs, and 16 g platinum on alumina packing pellets (or alternative catalyst). One records the weight and type of the catalyst, then places a glass wool plug in one end of the catalyst tube and mostly fills the tube with catalyst packing.

Then, one places the other glass wool plug inside the other end of the tube that was used to fill the tube with catalyst packing. The tube should now be essentially full of catalyst packing with glass wool plugs on each end.

One then places a mesh plate on each end of the tube and place a union over each end, thereby sandwiching the plate in between the union and the tube. One then secures the unions to each end of the tube with stainless steel nuts and ferrules.

To assemble the catalyst tube for use inside the probe, the spiking line is secured to one end of the catalyst tube with another stainless steel nut and ferrule, and the spiked-side sample line injection point is secured to the catalyst tube with a stainless steel nut and graphite ferrule. Then, one attaches ceramic insulation baffles around the spiking liner to prevent the spiking line from colliding with the spiked-side sample line. At this point one attaches thermocouples to the catalyst tube and half way down the spiking line.

One then slides the spiked line with the catalyst tube into the spiked-side sheath on the probe. One then inserts the probe into the oven and attaches the heating coils and thermocouples to their respective plugs.

We then attach the spiking line to the sulfur dioxide preheater in the oven, and attach the heated jumper to the spiked-side sample line. We attach the sulfur dioxide injection input on the oven to the mass flow controller/mixer exit, and attach another line from the mass flow controller/mixer exit going to the probe tip. This gas line will be used to bypass the catalyst when needed.

There should be a valve that will direct the mass flow controller/mixer exit to the catalyst or to the probe tip (catalyst bypass). We attach the heated jumper to the input of the FTIR, and vent the FTIR to a fume hood. We make sure that the vent line can drain into an acid waste container since sulfuric acid will condense in the vent line.

The mass flow controller is set up to mix two gasses. In order for the conversion of sulfur dioxide to sulfur trioxide to take place, an excess of oxygen needs to be present in the catalyst tube. This means that a sulfur dioxide cylinder (which is usually balanced in nitrogen when commercially supplied) needs to be further diluted with air or some other oxygen source via the mass flow controller/mixer.

Alternatively, one can obtain a cylinder of sulfur dioxide pre-balanced with air, and just use one cylinder instead of mixing sulfur dioxide balanced with nitrogen and air. However, the catalyst still needs to purged with air between operation, so a separate air cylinder must be available regardless.

At this point, the catalyst tube must be seasoned, so the parts are assembled as shown in FIG. 2. One then pre-heats the equipment (800° F. for the catalyst, 600° F. for the oven, and 350° F. for the heated jumper). One then bypasses the catalyst tube and flows dry air from an air cylinder into the FTIR at the spiking flow rate (e.g. two liters per minute). The FTIR system is then set to show zero levels of sulfur trioxide and sulfur dioxide.

One then verifies a seasoning concentration of sulfur dioxide supply at two liters per minute at 100 ppm sulfur dioxide. After this, one begins to flow sulfur dioxide through the catalyst and records sulfur trioxide readings on the FTIR. This flow continues until the sulfur trioxide readings on the FTIR rise and then level out. This typically takes more than ten hours, depending on the catalyst type.

Once the sulfur trioxide readings are constant on the FTIR, one can purge the catalyst with cylinder air. This ensures that no extra sulfur dioxide remains in the catalyst tube when it is cooling down or moved. The saturation point of the alumina in the catalyst tube increases when its temperature decreases, so any extra sulfur dioxide in the catalyst tube will become adsorbed to the alumina when it cools down. This might create an uneven conversion rate when heating the catalyst tube back up to operating temperature again.

It is not advisable to flow sulfur dioxide through the catalyst tube when it is not at operating temperature. Note that care must be taken in venting the FTIR as released sulfur trioxide will likely condense to sulfuric acid one it has left the FTIR and come in contact with moisture.

Once the catalyst tube is seasoned, the equipment is now ready to use for monitoring flue gas. We assemble the equipment at the test location as shown in FIG. 1.

Here we slide the spiked line with the catalyst tube into the spiked-side sheath on the probe. We then slide the unspiked-side sample line into the unspiked-side sheath on the probe. Before attaching the oven, the probe can be inserted into the flue duct and secured. We then insert the probe into the oven and attach the heating coils and thermocouples to their respective plugs, and attach the spiking line to the sulfur dioxide pre-heater in the oven.

We then attach the mass flow controller and cylinder gases to the sulfur dioxide input on the oven, insert the particulate filter housings into the oven, and attach them to the spiked-side and unspiked-side sample lines. We then attach the sulfuric acid condensers to the exit of the filter housings for both spiked and unspiked trains.

We then attach the impinger sets for each train and ice them down, and the exit of the impinger sets to the meters and pumps. We then run leak check for each train. Since the probe may likely be in the duct, leak checks can be performed from the downstream fitting of the sample liners. Silicone grease is acceptable to use as a vacuum sealant.

We then begin to purge the catalyst tube with gas from the mass flow controller/mixer. Since the vacuum pumps are not running at this point, the purge will flow out the probe tip into the duct. For the first field spiking procedure, we then continue to purge the catalyst at the spiking flow rate when the run starts.

We then begin to purge the catalyst tube with gas from the mass flow controller/mixer. Since the vacuum pumps are not running at this point, the purge will flow out the probe tip into the duct. We then continue to purge the catalyst at the spiking flow rate when the run starts.

At this point, we begin sampling at a constant rate with both trains simultaneously. This will cause the spike purge to be sucked into the spiked-side train. Five minutes into the run, we begin to flow sulfur dioxide through the catalyst tube to generate the sulfur trioxide spike. We then continue to spike the spiked-side train until five minutes before the run is over. At that point we begin purging the catalyst with air. When finished with the run, we continue to purge the catalyst with air. Leak check each train again.

An alternative procedure is possible to allow dynamic spiking using a catalyst that takes significant time to begin generating a stable amount of sulfur trioxide. This may be needed with catalysts that have porous structures (e.g. alumina-based) where generated sulfur trioxide may be caught in the porous structure and take significant time to be ultimately released. This gradual increase of sulfur trioxide generation we call ramping.

After ramping, sulfur trioxide generation remains stable at a known concentration and can be used to dynamically spike a sample. Purging the catalyst with air takes an equally significant amount of time to remove all caught sulfur trioxide from the porous catalyst. Therefore, using a ramping catalyst does not allow for the first and last five minutes of the sampling run to be used for purging the catalyst. Instead, this alternative procedure calls for pre-ramping the sulfur trioxide generation before the run begins.

To pre-ramp, we flow sulfur dioxide through the catalyst to generate sulfur trioxide before the run begins to allow the sulfur trioxide generation to ramp up. Since the sampling trains are not pulling sample through the system, the sulfur trioxide generated from ramping is flowing out of the probe tip.

Once sulfur trioxide generation is stable (determined by previous pre-ramp times), the run may start by beginning to pull flue gas with both trains. The catalyst will generate a known amount of sulfur trioxide at a constant rate throughout the entire duration of the run and spike one of the sample trains. Sulfur trioxide generation will remain at a stable level until the conclusion of the run and sampling ceases. At this point, the generated sulfur trioxide will flow out the probe tip again (the same as before the run) while the sample trains are recovered for sulfuric acid content. When the sulfur trioxide/sulfuric acid testing has finished, the catalyst can be purged with air.

A number of different spiking ratios and concentrations can be used to investigate sources of method bias. The amount of purge at the beginning and the end of each run may be shorter or longer than five minutes based on catalyst properties. The dynamic spiking system probe and oven may be used in vertical or horizontal ports.

The present invention provides a compact and efficient assembly for measuring the concentration of sulfur trioxide/sulfuric acid in flue gas, and adjusting for measurement bias. For example, if one had a measurement of 20 mg sulfate from the sulfuric acid condenser in the unspiked line, and spiked a total of 15 mg sulfate in the spiked line, yet had a result of 30 mg sulfate from the sulfuric acid condenser in the spiked line, one would conclude that system bias is causing part (one third) of the sulfur trioxide to be missed. This would lead one to conclude that the flue gas had a higher level of sulfur trioxide than what was collected in the unspiked line (e.g. 30 mg instead of 20 mg).

By dynamically spiking one sampling train while simultaneously running another sampling train, one can validate the test method used at that particular location. One can then identify how much bias the test method has at each individual location by comparing the expected recovery of the spike to the actual recovery of the spike. This is significant because different locations may have different biases due to different particulate conditions or moisture conditions.

For example, if sulfuric acid testing is required in a wet stack (saturated stream), moisture might be collecting inside the testing equipment and absorbing sulfur trioxide before it can reach the sulfur trioxide condenser (causing a low bias).

By dynamically spiking one train, we can determine the amount of bias that location has on the test method. This validates the test method at that location.

Also, the dual-train setup can be used as a co-located test method. By not flowing any gas through the catalyst, each train becomes an unspiked train during runs. The resulting sulfate results from the sulfuric acid condensers may be compared to assess the precision of the test method.

While a preferred embodiment of the present invention has been described, it should be recognized that many other embodiments are possible without departing from the spirit and scope of the invention. For example, the probe could be supplied with a third, fourth or more sampling lines to monitor other gas(es) of interest. Further, the precise catalyst used, and conditions for use thereof, can be varied if desired.

Hence, to ascertain the full scope of the invention the claims which follow should be referenced.

INDUSTRIAL APPLICABILITY

The invention provides improved monitoring equipment for monitoring sulfur trioxide/sulfuric acid levels in flue gas, and methods for use thereof.

We claim:

1. A system for monitoring sulfur trioxide/sulfuric acid levels in an emission stream comprising sulfur trioxide and water vapor flowing through an exhaust, the system comprising:
a probe positionable adjacent to the exhaust to be able to extract essentially simultaneously a first supply of sample gas from the exhaust and a second supply of sample gas from the exhaust, wherein the second supply of sample gas is separate from the first supply of sample gas, the probe comprising the following elements housed within an outer probe shell:
(i) an unspiked line for carrying the first supply of sample gas,
(ii) a spiking line for carrying the second supply of sample gas,
(iii) a catalyst for converting $SO_2$ gas to $SO_3$ gas,
(iv) an inlet line for supplying $SO_2$ gas of a known quantity to the catalyst,
(v) a heating coil positioned adjacent to the catalyst,
(vi) a thermocouple,
(vii) a carrier line for adding $SO_3$ gas generated at the catalyst to the second supply of sample gas in the spiking line to create a spiked gas, and
(viii) an outlet line for carrying the spiked gas to a connector to measuring equipment, the connector to the measuring equipment, and the measuring equipment in the form of the means for measuring as claimed below, being located outside the probe;
the system further comprising:
a condenser for condensing sulfuric acid in the first supply of sample gas carried by the unspiked line;
a condenser for condensing sulfuric acid in the spiked gas carried by the outlet line;
means for measuring sulfuric acid content in the first supply of sample gas carried by the unspiked line; and
means for measuring sulfuric acid content in the spiked gas carried by the outlet line;
whereby the system is configured such that a comparison of the measuring of the sulfuric acid content in the first supply of sample gas carried by the unspiked line with the measuring of sulfuric acid content in the spiked gas carried by the outlet line can help validate the system.

2. The system of claim 1, wherein the heating coil is capable of heating the catalyst to a temperature above 750° F.

* * * * *